(12) United States Patent
Piantoni et al.

(10) Patent No.: US 10,028,863 B2
(45) Date of Patent: Jul. 24, 2018

(54) MACHINE FOR MAKING ABSORBENT SANITARY ARTICLES

(71) Applicant: GDM S.p.A., Bologna (IT)

(72) Inventors: Matteo Piantoni, Albino (Bergamo) (IT); Alberto Perego, Milan (IT)

(73) Assignee: GDM S.p.A., Bologna (IT)

( * ) Notice: Subject to any disclaimer, the term of this patent is extended or adjusted under 35 U.S.C. 154(b) by 0 days.

(21) Appl. No.: 15/794,097

(22) Filed: Oct. 26, 2017

(65) Prior Publication Data

US 2018/0042781 A1 Feb. 15, 2018

Related U.S. Application Data

(62) Division of application No. 14/343,294, filed as application No. PCT/IB2012/054761 on Sep. 13, 2012, now Pat. No. 9,827,148.

(30) Foreign Application Priority Data

Sep. 21, 2011 (IT) .............................. BO2011A0537

(51) Int. Cl.
  *A61F 13/00* (2006.01)
  *A61F 13/15* (2006.01)
  *B29C 65/00* (2006.01)
(52) U.S. Cl.
  CPC .. *A61F 13/15739* (2013.01); *A61F 13/15772* (2013.01); *B29C 66/96* (2013.01)
(58) Field of Classification Search
  CPC ............... B29C 66/96; A61F 13/15739; A61F 13/15772; A61F 2013/1578; A61F 2013/15788; A61F 2013/15796
  (Continued)

(56) References Cited

U.S. PATENT DOCUMENTS

| 4,837,715 A | 6/1989 | Ungpiyakul et al. |
| 5,930,139 A | 7/1999 | Chapdelaine et al. |

(Continued)

FOREIGN PATENT DOCUMENTS

| CN | 1668261 A | 9/2005 |
| JP | 2012501938 A | 1/2012 |

(Continued)

OTHER PUBLICATIONS

Office Action dated Jan. 24, 2017 issued by Japanese Patent Office from related Japanese application No. 2014-557141 [14370429].

(Continued)

*Primary Examiner* — George Koch
(74) *Attorney, Agent, or Firm* — Shuttleworth & Ingersoll, PLC; Timothy Klima

(57) ABSTRACT

A machine for making absorbent sanitary articles, where each article includes components progressively positioned relative to each other and assembled along a production line. The machine includes a programmable electronic controller device having a shift register, at least one optical inspection system connected to the programmable electronic controller device, and an operator interface connected to the electronic controller. The programmable electronic controller device generates a machine sync signal, a trigger signal for activating the optical inspection system in phase with the sync signal and a shift register shift command. The optical inspection system receives the trigger signal and has a defined maximum response time which produces at least one band of uncertainty. The operator sets with the operator interface the instant of activating the shift register shift command outside the band of uncertainty and between two consecutive sync signals defining a machine step.

9 Claims, 5 Drawing Sheets

(58) Field of Classification Search
USPC .......................... 156/64, 269; 700/122, 129
See application file for complete search history.

(56) References Cited

U.S. PATENT DOCUMENTS

| | | |
|---|---|---|
| 6,845,283 B2 | 1/2005 | Popp et al. |
| 2003/0169433 A1 | 9/2003 | Koele et al. |
| 2004/0030432 A1 | 2/2004 | Popp et al. |
| 2009/0020211 A1 | 1/2009 | Andrews et al. |
| 2010/0305738 A1 | 12/2010 | DeBruler et al. |
| 2010/0305740 A1 | 12/2010 | Kent et al. |

FOREIGN PATENT DOCUMENTS

| | | |
|---|---|---|
| WO | WO0040195 A1 | 7/2000 |
| WO | WO0156525 A1 | 8/2001 |
| WO | WO2007105938 A1 | 9/2007 |
| WO | WO2010030483 A1 | 3/2010 |

OTHER PUBLICATIONS

International Search Report and Written Opinion dated Jun. 21, 2013 from related app No. PCT/IB2013/051111 [14370429].
Office Action dated Nov. 4, 2014 issued by Intellectual Property Office of the People's Republic of China for related Chinese app No. 201280045752.9.
International Search Report dated Jul. 12, 2013 from counterpart International App No. PCT/IB2012/054761.

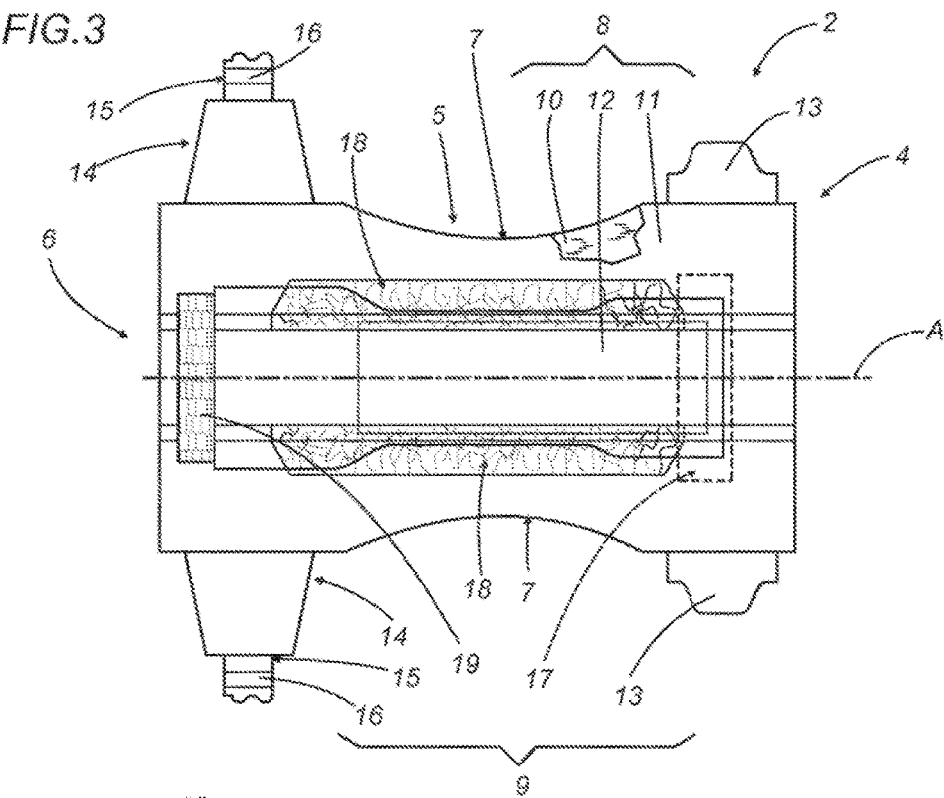
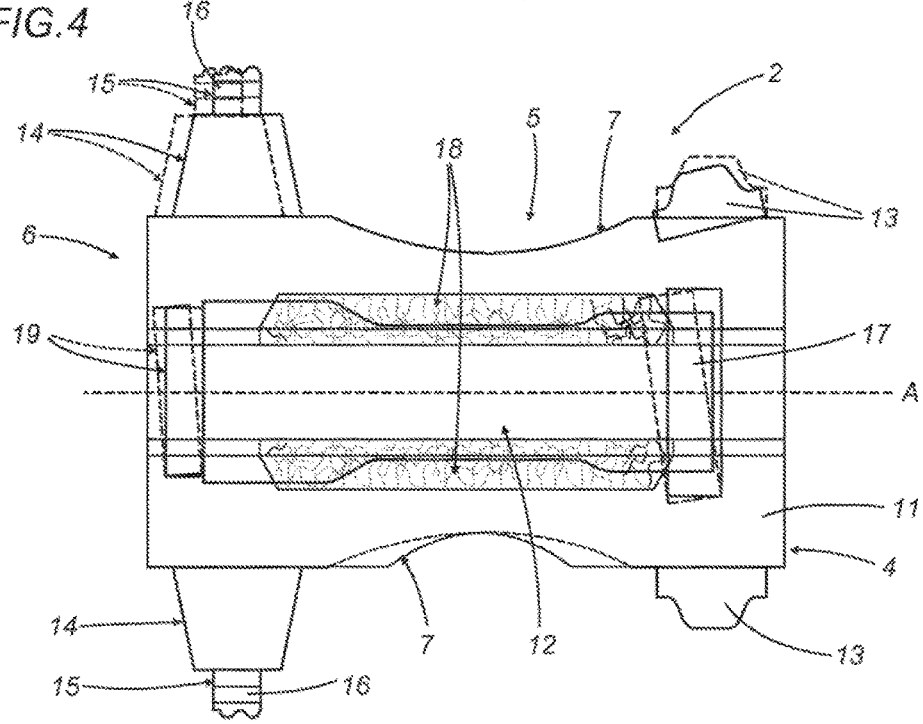

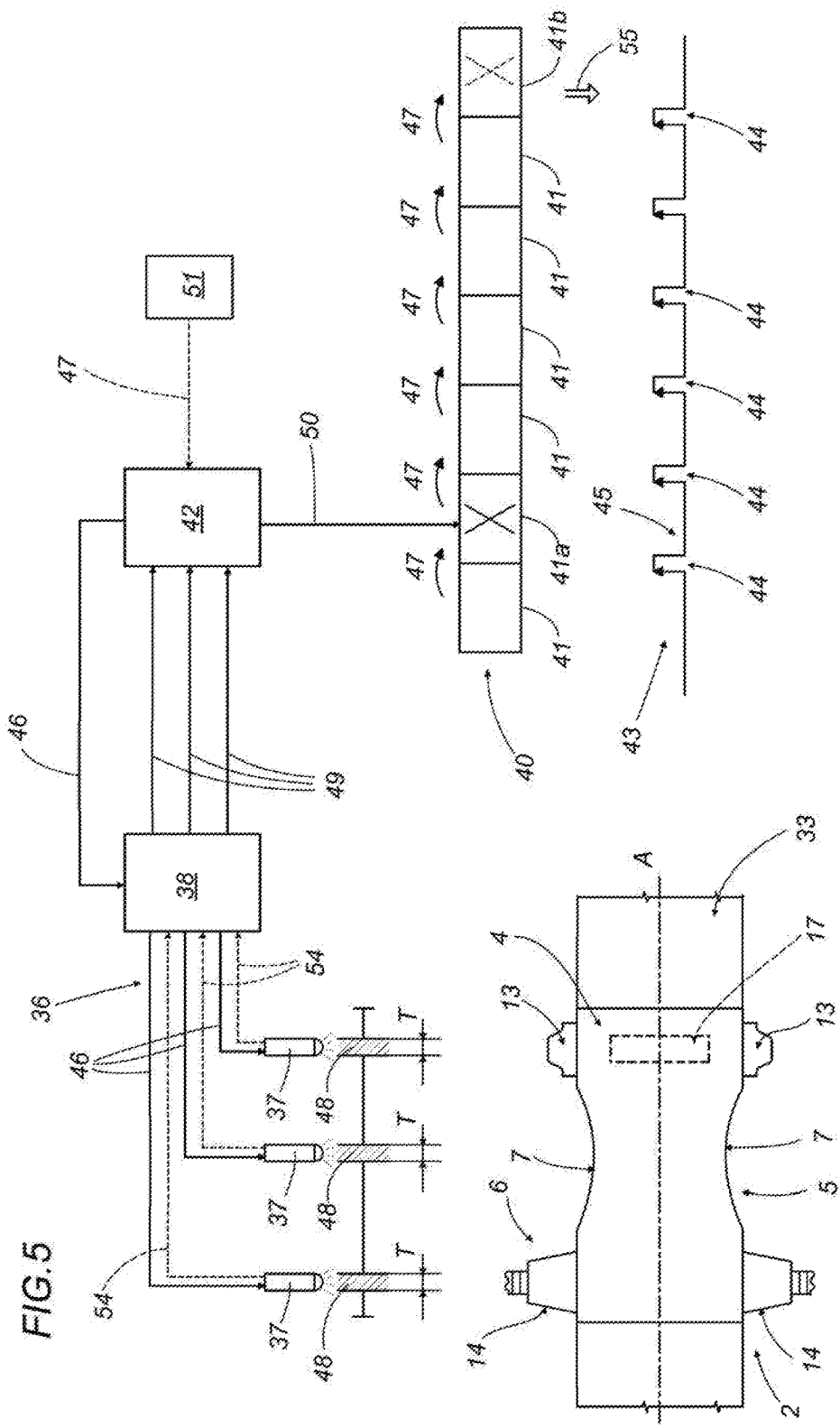

US 10,028,863 B2

MACHINE FOR MAKING ABSORBENT SANITARY ARTICLES

This application is a divisional of U.S. patent application Ser. No. 14/343,294 filed Mar. 6, 2014, now U.S. Pat. No. 9,827,148 B2, which is a National Phase of International Application PCT/I62012/054761 filed Sep. 13, 2012 which designated the U.S. and that International Application was published under PCT Article 21(2) in English.

This application claims priority to Italian Patent Application No. BO2011A000537 filed Sep. 21, 2011, which application is incorporated by reference herein.

TECHNICAL FIELD

This invention relates to a machine for making absorbent sanitary articles.

More specifically, the invention relates to a machine for making absorbent sanitary articles such as nappies for children and adults, sanitary pads and the like.

BACKGROUND ART

As is known, a machine for making absorbent sanitary articles has a production line along which advances a continuous web of absorbent material consisting of a layer of permeable material (of non-woven fabric) laid over a layer of impermeable material, with absorbent padding interposed between the two layers. As the continuous web advances along the production line, additional components are applied to the continuous web, such as, for example, lateral stretch bands, lateral sealing flaps, a rear stretch tape and a front band designed to engage the lateral sealing flaps.

Once these additional components have been applied to the continuous web, a continuous succession of absorbent sanitary articles is formed and a cutting device located downstream of the production line divides the continuous succession into individual absorbent articles which are then folded and packed.

Every line for the production of absorbent sanitary articles also comprises at least one rejection station, located downstream of the cutting device, which rejects the defective absorbent sanitary articles, that is to say, the absorbent articles which do not meet specified quality parameters.

Checking for defective absorbent sanitary articles is carried out by a software logic built into an electronic controller of the making machine.

The machine controller, besides generating a machine sync signal 100, is designed to assign information about the article being processed to a shift register 101, as illustrated in FIG. 1. The shift register 101 is defined by a plurality of steps 102, each associated with a time position of an absorbent article being processed along the production line.

In order to identify the defective absorbent articles, the production line comprises a plurality of check points for checking that the absorbent sanitary article has been made up correctly. These check points are connected to the machine controller and are designed to detect and flag any production defects in each absorbent article being made.

The moment a check point detects and flags a production defect to the machine controller, the latter assigns that information item to a particular step 102 of the shift register 101. The step 102 is shifted along the shift register until reaching a last position 108 corresponding to the rejection station where the defective absorbent sanitary article is rejected.

At the check points, generally speaking, there are optical inspection systems, such as photocells, or vision systems comprising, for example, commercial video cameras.

A photocell is an inspection component which generates a random signal 103 which is asynchronous relative to the machine sync signal 100. The asynchronous signal 103 of the photocell is defined as ambiguous 104 when it is concurrent with the machine sync signal 100 and unambiguous 105 when it is not concurrent with the machine sync signal 100.

If the photocell signal is unambiguous 105, relative to the machine sync signal 100, the machine controller assigns the defective article information item to a particular step 102 of the shift register 101, so that the defective absorbent sanitary article is certain to be rejected when it reaches the rejection station.

If the photocell signal is ambiguous 104, relative to the machine sync signal 100, an uncertainty window is created and the machine controller is unable to assign the defective article information item to a particular step 102 of the shift register 101. In this case, the machine controller assigns the information item to two or more steps 102 of the shift register 101 in order for the defective absorbent sanitary article to be certainly identified and rejected. Unfortunately, however, that means that absorbent sanitary articles which are not defective are rejected together with the defective article at the rejection station.

From the above, it may be inferred that every time the photocell signal is ambiguous 104 relative to the machine sync signal 100, a significant quantity of good products are rejected together with the defective products, which translates as a considerable waste of raw materials.

Unlike photocells, vision systems are stable response systems since they are controlled by a trigger pulse 106 generated by the machine controller.

From the moment the vision system receives the trigger pulse 106, it has a maximum response time to flag a defect, if any, thus defining a band of uncertainty 107 which may be concurrent with the machine sync signal 100 and hence ambiguous, as illustrated in FIG. 1. Under these conditions, the machine controller is unable to determine a specific step 102 of the shift register 101 to assign the defective article information item to and, as in the case of the ambiguous photocell signal 104, assigns the information item to two or more steps 102 of the shift register 101 so that the defective absorbent sanitary article is certainly identified and rejected.

Even the use of a vision system does not solve the problem of rejecting sanitary articles which are not defective. Thus, every time the band of uncertainty 107 is ambiguous relative to the machine sync signal 100 a considerable number of good products are rejected together with the defective products.

DISCLOSURE OF THE INVENTION

The aim of this invention is to provide a machine for making absorbent sanitary articles and which rejects only the defective product, without having to reject any products which are not defective, thus minimizing the number of products which the machine must strictly reject.

The above mentioned technical purpose and aims are achieved by a machine having the technical features described in the independent claim 1.

BRIEF DESCRIPTION OF THE DRAWINGS

Further features and advantages of this invention are more apparent in the description below, with reference to a preferred, non-limiting, embodiment of a machine as illustrated in the accompanying drawings, in which:

FIG. 3 illustrates an absorbent sanitary article without production defects, made by the machine illustrated in FIG. 2;

FIG. 4 shows the absorbent sanitary article of FIG. 3 with some production defects;

FIG. 5 is a block diagram representing the inspection section of the machine of FIG. 2;

DETAILED DESCRIPTION OF THE PREFERRED EMBODIMENTS OF THE INVENTION

Figure 1:
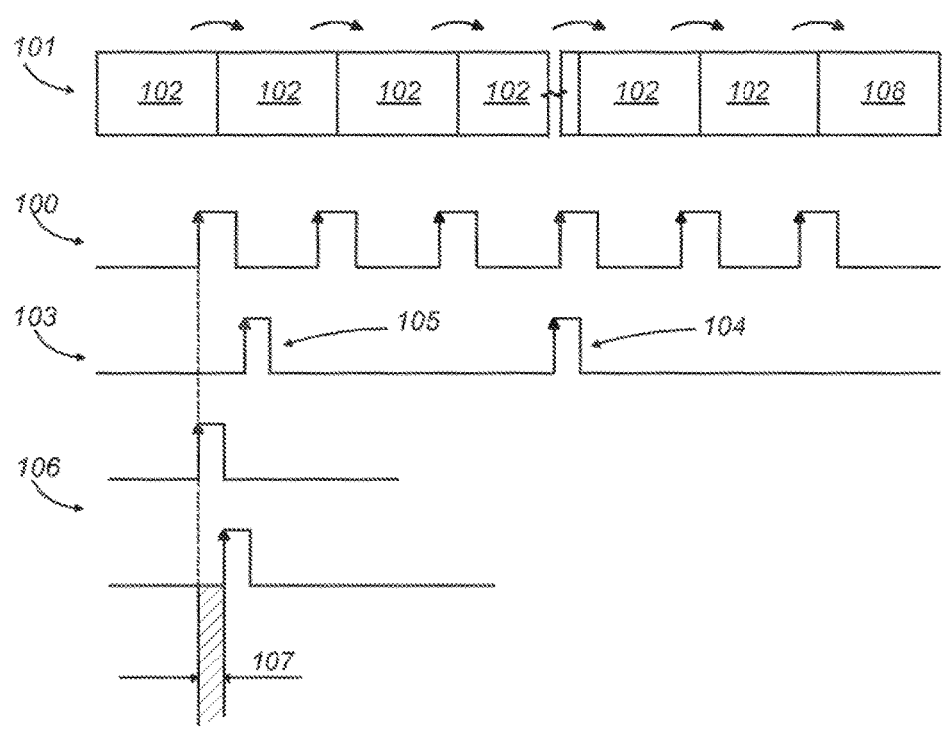
FIG. 1 illustrates control signals and information in a prior art making machine.
Figure 2:
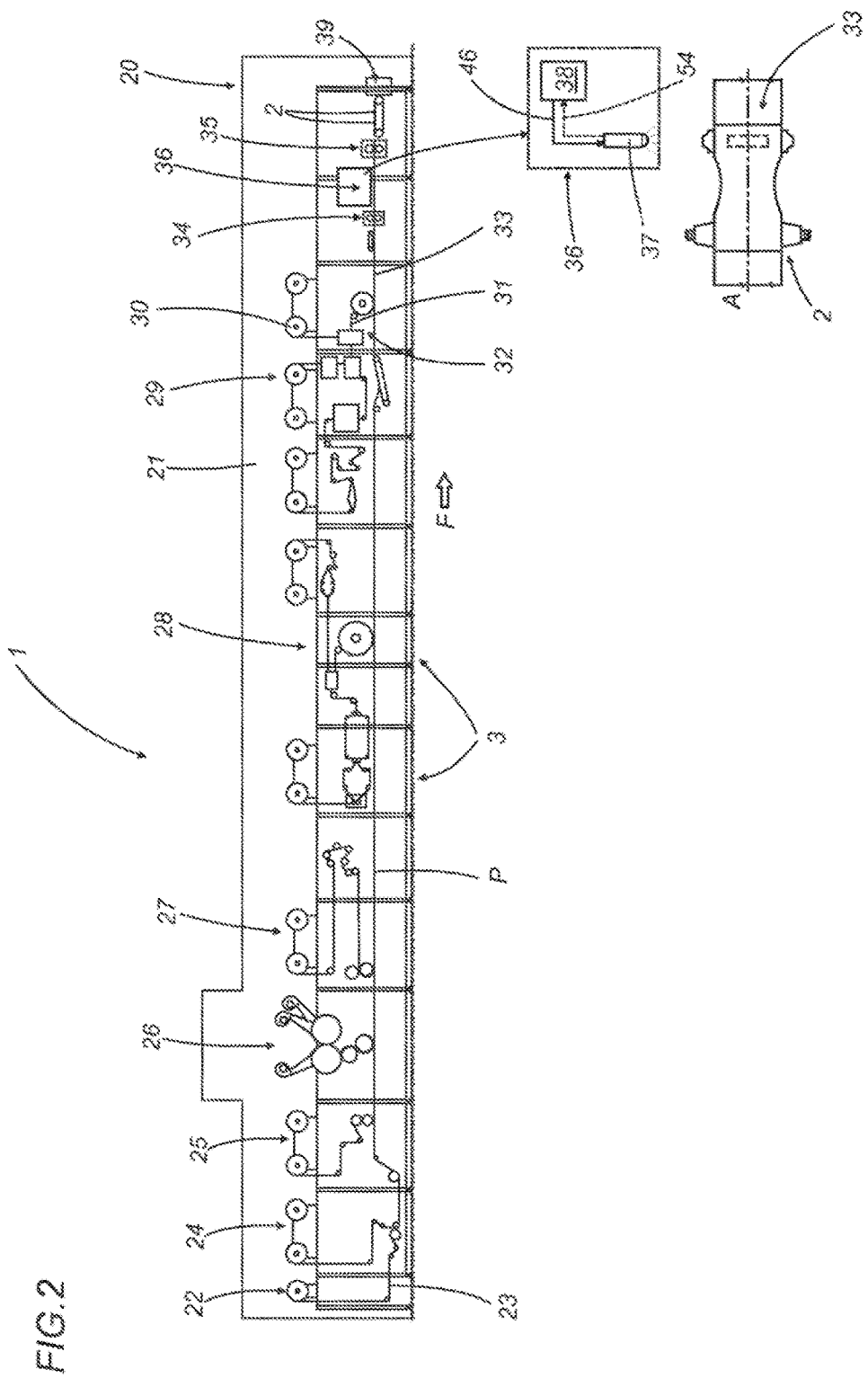
FIG. 2 is a schematic front view of a making machine according to this invention.

As shown in FIG. 2, the numeral 1 denotes a machine for making absorbent sanitary articles 2 and comprising a substantially horizontal production line 3 along which the absorbent sanitary article 2 is made.

The article 2 has a substantially rectangular shape and comprises, in a line along its longitudinal axis A, a front portion 4, a central portion 5 and a rear portion 6, as illustrated in FIG. 3.

At the central portion 5 the article 2 has a recess 7, or thigh opening, defined by two arcuate sections which are symmetrical about the axis A.

The articles 2 are composed of a plurality of components, which can be broadly divided into main components 8, or basic parts, and accessory components 9, or accessory parts.

The main components 8 include a sheet 10 of impermeable material and a sheet 11 of permeable material (non-woven fabric) used to make the outside face and the inside face of the article 2, respectively.

The sheets 10 and 11 are laid over each other and interposed between them there is another main component constituted by an absorbent padding 12.

The accessory components 9, which may vary in number and shape, are described below with reference to the sanitary article 2 illustrated in FIG. 3.

The numeral 13 denotes two shaped flaps fixed to the inside face of the sheet 10 and extending from the front portion 4 transversely to the axis A.

The numeral 14 denotes two shaped flaps, parallel to the flaps 13, extending from the rear portion 6.

Applied to each of the flaps 14 there is a tab 15 provided with an adhesive strip 16 designed to adhere, in use, to a corresponding front strip 17 applied to the front portion 4 of the outside face of the sheet 10.

Laterally sealed to the sheet 11 of permeable material there are two strips 18 of impermeable material for thickening and expanding its longitudinal edges.

A further accessory component 9 is a stretch tape 19 applied transversely of the axis A to the inside face of the rear portion 6 of the sheet 10.

With reference to FIG. 2, the machine 1 comprises a base 20 substantially in the shape of a parallelepiped and delimited at the front by a vertical wall 21.

The wall 21 constitutes a support for a plurality of operating units. These operating units comprise cutting devices and sealing devices, as well as units for unwinding the materials making up the article 2 from respective rolls mounted on axes transversal to the wall 21.

The making machine 1 is a cyclic production machine of continuous type, that is to say, at each machine cycle, one finished absorbent sanitary article 2 is made.

At its infeed, the machine 1 comprises a unit 22 for unwinding a continuous web 23 of impermeable material which, after being cut into lengths, constitutes the sheets 10.

The continuous web 23 runs along a horizontal path P of the production line 3, in the direction indicated by the arrow F, through the operating units where the article 2 is progressively made up and completed by successively adding the basic components 8 and the accessory components 9.

At a first operating unit 24, the front strip 17 transversal to the axis A is applied in known manner, using an adhesive substance, to the front portion of the outside face of each length of the of the web 23 corresponding to an absorbent article 2.

At a second operating unit 25, the tape 19 of stretch material is applied transversely to the axis A in known manner, using an adhesive substance, to the rear portion of the inside face of each length of the of the web 23 corresponding to an absorbent article 2.

At a third operating unit 26, the absorbent padding 12 is applied to the central zone of each length of the web 23.

Downstream of the operating unit 26 the web 23 passes through a fourth operating unit 27 where the two front flaps 13 are made and hence applied to each length of the web 23.

Downstream of the operating unit 27, along the path P, there is a fifth operating unit 28 where the two rear flaps 14, each of which is provided with a respective grip tab 15, are made and applied to the web 23.

Downstream of the unit 28, the wall 21 supports, in proximity of its right-hand end, a sixth operating unit 29 comprising a unit 30 for unwinding a web 31 of permeable material.

At a sealing station 32, the web 31 of permeable material and the web 23 of impermeable material are sealed to each other along the respective edges to make a continuous web 33 which will eventually define the articles 2. In other words, the continuous web 33 is a continuous succession of finished articles 2 complete with the basic parts 8 and the accessory parts 9.

The continuous web 33 passes through a further operating unit 34, where each length of the web 33 is cut in such a way as to make two substantially semicircular portions that will constitute the recesses 7 of the absorbent article 2.

Downstream of the operating unit 34, a cutting device 35 transversely divides the web 33 into the individual finished articles 2.

At the end of the production line 3, downstream of the cutting device 35, there is at least one rejection station 39 for rejecting absorbent articles 2 which are defective. The rejection station 39 is located downstream of the cutting device 35. That means the rejection station 39 may be located upstream or downstream of a folding station, not illustrated, where each single absorbent article 2 is folded.

The making machine 1 comprises at least one optical inspection system 36 for checking the quality of the articles 2 as they feed out of the production line 3.

The optical inspection system 36 is designed to detect and flag production defects in the finished absorbent article 2.

The optical inspection system 36 comprises at least a video camera 37 for capturing at least one image 54 of the absorbent article 2 and a unit 38 for acquiring and processing images of the absorbent article 2 and connected to the video camera 37.

In the preferred embodiment, the image capturing video camera 37 is a linear video camera. Further, the optical inspection system 36 is a vision system.

More specifically, at least one video camera 37 is located at the outfeed of the production line 3. In effect, the video camera 37 located at the end of the production line 3 inspects the absorbent article 2 complete with the basic components 8 and the accessory components 9.

As illustrated in FIG. 2, the video camera 37 is mounted to face the continuous web 33 of articles 2 while they are still joined to each other, upstream of the cutting device 35, so as to capture at least one image 54 of each article 2 before the latter is cut off from the continuous web 33.

As the continuous web 33 advances along the path P, the linear video camera 37 inspects the web 33 with a field of vision spanning the full width of the web 33.

Alternatively, the video 37 might be located downstream of the cutting device 35 in order to capture at least one image 54 of a single finished article 2 after it has been cut off from the continuous web 33.

The image acquisition and processing unit 38 analyses the images and thereby assesses whether the predefined quality parameters of the absorbent article 2 fall within respective tolerance ranges. If one or more of the quality parameters are outside the respective tolerance range, the acquisition and processing unit 38 flags the presence of a production defect in the absorbent article 2.

Production defects or faults, examples of which are given below, may occur during the application and forming of the base parts 8 and accessory parts 9.

FIG. 4 shows some of the components of the absorbent article 2 positioned incorrectly, as indicated by the dashed lines, compared to the correct positions indicated by the solid lines, such as for example, the incorrectly oriented front strip 17 and stretch tape 19, the incorrectly positioned the flaps 13 and 14 and the incorrectly shaped recess 7.

These production defects, once detected and flagged by the acquisition and processing unit 38 cause the finished absorbent article 2 to be rejected when it reaches the rejection station 39 of the production line 3.

Another example of a production defect which causes the article 2 to be rejected is the absence of one or more basic parts 8 and/or accessory parts 9.

In terms of logical representation, the making machine 1 is mapped by a single shift register 40, as illustrated in FIG. 5.

The shift register 40 or "chain" is represented as a set of interconnected rectangular blocks. Each block 41 of the register 40 is defined as a step of the "chain".

Each step 41 of the shift register 40 corresponds to a time position of the absorbent article 2 being made up as it passes through each of the operating stations of the machine 1. More specifically, the information relating to the state of the product or of the material being processed along the production line 3 is stored in the shift register 40.

The making machine 1 is equipped with a programmable electronic machine controller device 42.

The electronic controller 42 applies a shift command 47 to the shift register 40.

The shift command 47 shifts each step 41 in a single direction until reaching the last block 41b of the "chain" corresponding to the moment the finished absorbent article 2 is at the rejection station 39.

The electronic controller 42 generates a machine sync signal 43. More specifically, the machine sync signal 43 is generated by an encoder.

The sync signal 43 has a train of control pulses 44 with a phase, a duration and a number of repetitions which depends on the process cycle of the machine 1.

More specifically, two consecutive pulses 44 of the sync signal 43 define a machine step 45 which corresponds to one position of the absorbent article 2 being made up along the production line 3.

The vision system 36 is connected to the programmable electronic controller device 42.

More specifically, the vision system 36 is activated by the programmable electronic controller device 42 which generates a trigger signal 46 of the vision system 36 in phase with the machine sync signal 43.

From the moment it receives the trigger signal 46, the vision system 36 has maximum defined response time for flagging the presence of a production defect, if any, of the article 2.

The maximum response time T of the vision system 36 creates a band of uncertainty 48, or uncertainty window, defined temporally from the instant in which the vision system 36 receives the trigger signal 46 to the instant in which the vision system flags the defect, if any.

The duration of the band of uncertainty 48 is a known time quantity, since the maximum response time T is strictly dependent on the technology implemented in the vision system 36 itself, both by the video camera 37 and by the image acquisition and processing unit 38. More specifically, based on current technology, the band of uncertainty may have a duration of up to 4 msec.

Before the end of the band of uncertainty 48, the image acquisition and processing unit 38 sends a rejection signal 49 to the electronic controller 42. After receiving the rejection signal 49, the electronic controller 42 produces a rejection information item 50 to be assigned to a particular step 41 of the shift register 40. This step, labelled 41a, is shifted to the last block 41b of the register 40 in such a way as to generate a command 55 for rejecting the finished absorbent article 2 which is at the rejection station 39.

The vision system 36 inspects one or more areas of each length of the web 33 corresponding to a complete article 2. For example, the vision system 36 inspects the front portion 4 at the front strip 17 and flaps 13, the central portion 5 at the recesses 7 and the rear portion 6 at the flaps 14.

In this case, the vision system 36 generates three distinct bands of uncertainty 48, each associated with the defects of the respective portion 4, 5 and 6 of the article 2.

In order to inspect the chosen areas of the article 2, the vision system 36 may use a single video camera 37 or a plurality of video cameras 37, each dedicated to an inspection area. In this specific case, three distinct video cameras 37 are used, each dedicated to inspecting the respective portion 4, 5 or 6. In an alternative embodiment, each video camera 37 is dedicated to the optical inspection of certain basic parts 8 and/or accessory parts 9 at a certain position along the production line 3.

More specifically, if the vision system 36 comprises a plurality of video cameras 37, these are activated within the same machine step 45, each generating a band of uncertainty 48.

If the vision system 36 comprises a single video camera 37, on the other hand, the camera is activated at least once within the same machine step 45, generating a respective band of uncertainty 48 associated with the corresponding activation.

Consequently, one machine step 45 defined by two consecutive sync pulses 44 has at least one band of uncertainty 48.

Figure 6:
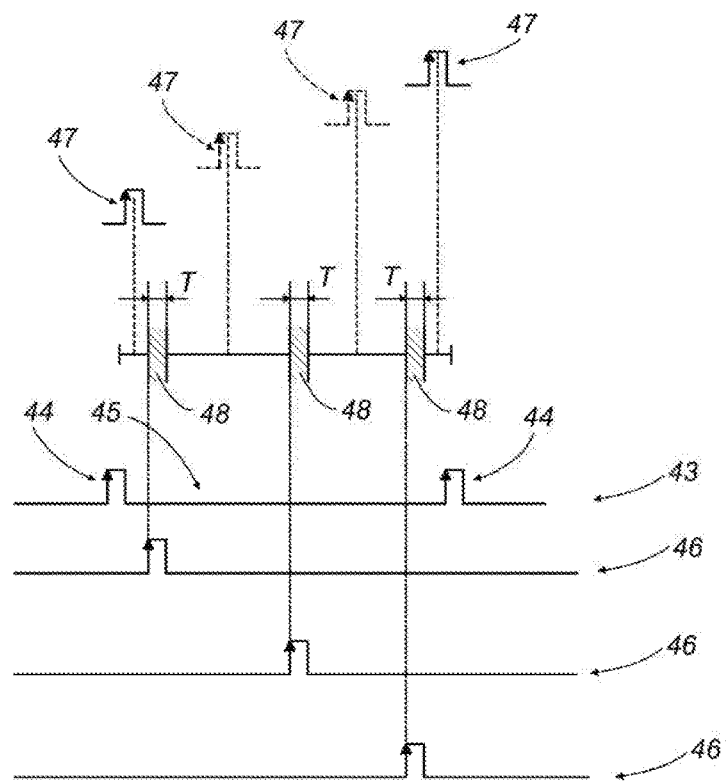
FIG. 6 shows a series of control and checking signals generated by the inspection section of FIG. 5.

In order to prevent the bands of uncertainty 48 from being concurrent with the shift register 40 shift command 47, the operator sets with an operator interface 51 connected to the electronic controller 42, the instant of activating the shift register 40 shift command 47 within a machine step 45, outside the band/bands of uncertainty 48, as illustrated in FIG. 6.

That way, the shift register 40 shifts either before or after the band/bands of uncertainty 48 so that the step 41*a* of the shift register 40 which the article 2 defective information item must be assigned to is certain.

The operator interface 51, comprising a touch screen or a screen keyboard, is normally implemented by a dedicated software program.

Figure 7:
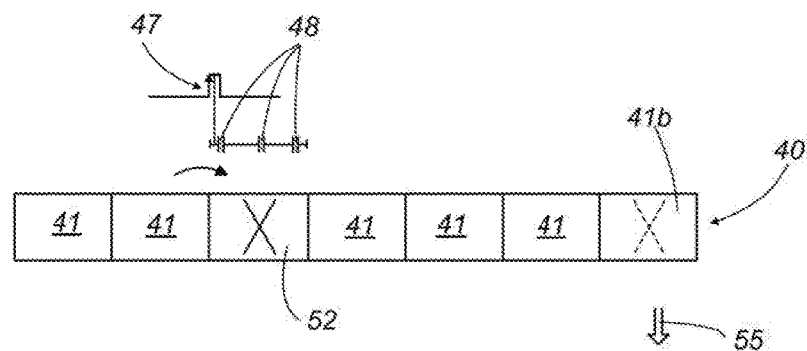
FIG. 7 shows a first variant of FIG. 6.

As illustrated in FIG. 7, the operator sets with the operator interface 51 the activation of the shift register 40 shift command 47 before the band of uncertainty 48, so that the shift register 40 shifts one step 41 before the vision system 36 is activated. After the band of uncertainty 48 has elapsed and the defect has been flagged by the vision system 36, the electronic controller 42 assigns the rejection information item 50 to the corresponding step 52 of the register 40.

Figure 8:
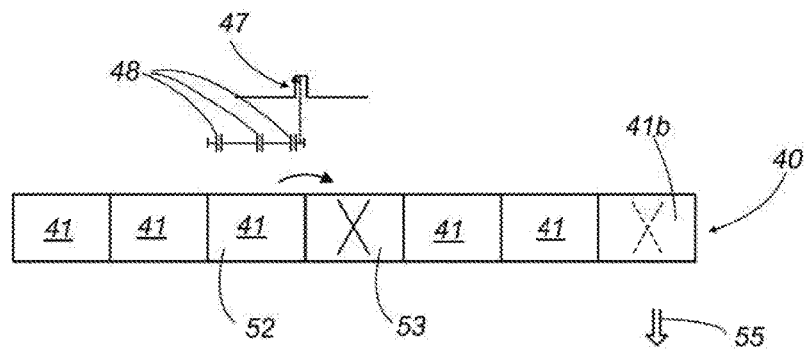
FIG. 8 shows a second variant of FIG. 6.

Alternatively, as illustrated in FIG. 8, the operator sets the activation of the shift register 40 shift command 47 after the band of uncertainty 48. In this case, the register 40 shifts one step 41 after the band of uncertainty 48 has elapsed and the electronic controller 42 assigns the rejection information item 50 to the corresponding step 53 of the register 40, after the step 52.

In both the cases of FIG. 7 and FIG. 8, only the defective absorbent article 2 is rejected at the rejection station 39 because the electronic controller 42 is able to assign the rejection information item 50 to a single step 52 or 53, since unlike the prior art, the shift command 47 is not concurrent with the band of uncertainty 48 of the vision system 36.

The operation of setting with the operator interface 51 the activation of the shift command 47 outside the band of uncertainty 48 is advantageous because it allows a single defective article 2 to be rejected even when the size of the absorbent articles 2 to be made is varied.

Indeed, the operator can set up the vision system 36 in such a way as to inspect certain areas of the absorbent article 2, according to the size of the article and the quality parameters to be met.

This setup operation involves setting with the operator interface 51 the trigger signals 46 of the vision system 36.

For example, in a machine 1 which makes 800 absorbent articles 2 per minute, the absorbent article 2 is 400 mm long and the operator, using the interface 51, sets the system so it inspects the areas of the article 2 at 100, 200 and 300 mm from a predetermined point 0, or origin, in order to check the basic parts 8 and/or the accessory parts 9 in those areas. Considering that the band of uncertainty 48 associated with each area inspected blacks out approximately 25 mm of the absorbent article 2, the operator can set the shift command 47 so it is activated either before or after all the bands of uncertainty 48.

Advantageously, the possibility of setting the activation of the shift register 40 shift command 47 not only guarantees that only the defective article 2 is rejected, without having to reject articles 2 which are not defective, but also allows the making machine 1 to be set up according to the size of the absorbent article 2. Setting up that way means that rejecting only the defective article 2 is possible for absorbent articles 2 of all sizes, differing in dimensions and possibly also in their accessory components 9.

The invention claimed is:

1. A machine for making absorbent sanitary articles, comprising:
   a programmable electronic controller device comprising a shift register,
   at least one optical inspection system connected to the programmable electronic controller device, the optical inspection system including an image acquisition and processing unit,
   an operator interface connected to the electronic controller;
   the programmable electronic controller device programmed to generate a machine sync signal, send a trigger signal to the optical inspection system to activate the optical inspection system in phase with the sync signal and apply a shift register shift command on the shift register;
   the optical inspection system receiving the trigger signal;
   at least one chosen from the programmable electronic controller device and the optical inspection system programmed and arranged to:
      set, from a moment the optical inspection system receives the trigger signal, a defined maximum response time for flagging a presence of a production defect, if any, of a sanitary article;
      the defined maximum response time creating a band of uncertainty, defined temporally from an instant in which the optical inspection system receives the trigger signal to an instant in which the optical inspection system flags the presence of the production defect, if any;
   the image acquisition and processing unit programmed to send, before an end of the band of uncertainty, a rejection signal to the programmable electronic controller device;
   the programmable electronic controller device programmed to produce, after receiving the rejection signal, a rejection information item to be assigned to a particular step of the shift register and to shift the particular step to a last block of the shift register, to generate a command for rejecting a finished sanitary article which is at a rejection station;
   an operator interface operably connected to the programmable electronic controller device, the programmable electronic controller device programmed to set an instant of activating the shift register shift command to be 1) within a machine step defined by two consecutive sync signals and to be 2) outside the band of uncertainty based an input from the operator interface.

2. The machine according to claim 1, wherein the instant of activating the shift register shift command is set before the band of uncertainty by the operator interface.

3. The machine according to claim 1, wherein the instant of activating the shift register shift command is set after the band of uncertainty by the operator interface.

4. The machine according to claim 1, wherein the optical inspection system comprises at a video camera for capturing at least one image of the absorbent article and wherein the image acquisition and processing unit is connected to the video camera.

5. The machine according to claim 4, wherein the video camera is a linear video camera.

6. The machine according to claim 1, wherein the optical inspection system is a vision system.

7. The machine according to claim 1, wherein the optical inspection system includes a video camera located in a proximity of an outfeed end of a production line of the absorbent sanitary articles.

8. The machine according to claim 4, wherein at least one chosen from the optical inspection system and the programmable electronic controller is programmed to activate the video camera at least once within a single step producing a corresponding band of uncertainty; the instant of activating the shift command being settable outside the band of uncertainty by the operator interface.

9. The machine according to claim 4, and further comprising a plurality of video cameras, wherein at least one chosen from the optical inspection system and the programmable electronic controller is programmed to activate the plurality of video cameras within a single step each producing a corresponding band of uncertainty; the instant of activating the shift command being settable outside the bands of uncertainty by the operator interface.

* * * * *